(12) United States Patent
Hatzfield et al.

(10) Patent No.: US 6,955,882 B2
(45) Date of Patent: Oct. 18, 2005

(54) METHOD FOR EASY CLONING AND SELECTION OF CHIMERIC DNA MOLECULES

(75) Inventors: Yves Hatzfield, Lille (FR); Valérie Marie-Noëlle Frankard, Brussels (BE); Anne-Marie Droual, Lille (FR)

(73) Assignee: CropDesign N.V., Ghent (BE)

( * ) Notice: Subject to any disclaimer, the term of this patent is extended or adjusted under 35 U.S.C. 154(b) by 23 days.

(21) Appl. No.: 10/349,782

(22) Filed: Jan. 23, 2003

(65) Prior Publication Data

US 2003/0143618 A1 Jul. 31, 2003

(30) Foreign Application Priority Data

Jan. 23, 2002 (EP) .............................. 02075373

(51) Int. Cl.⁷ ...................... C12Q 1/68; C12N 15/00
(52) U.S. Cl. ........................................ 435/6
(58) Field of Search .................. 435/6, 91.1, 69.1, 435/7.1, 91.2, 419, 189; 536/23.1, 24.1, 24.3; 530/370

(56) References Cited

U.S. PATENT DOCUMENTS

H1531 H * 5/1996 Blumentals et al. ........ 435/194

2002/0007051 A1 * 1/2002 Cheo et al. ................. 536/23.1
2004/0103453 A1 * 5/2004 Dudler et al. ............... 800/279

OTHER PUBLICATIONS

MultiSite Gateway™ Three Fragment Vector Construction Kit, Instruction Manual, Invitrogen™ Catalog No. 12537–023, Version A, Jul. 31, 2002.
Gateway ™ Cloning Technology Catalog, Life Technologies®.

* cited by examiner

*Primary Examiner*—Jeffrey Fredman
*Assistant Examiner*—Heather G. Calamita
(74) *Attorney, Agent, or Firm*—Ann R. Pokalsky; Dilworth & Barrese

(57) ABSTRACT

The invention provides a method that allows the construction of a chimeric and/or modified and/or reconstructed DNA molecule from two DNA fragments in a defined order and orientation, and to clone the molecule one step in a suitable vector using site specific recombination. No initial step of classical cloning via restriction enzymes is needed, in contrast to the classical recombination systems. This method allows the reliability of the recombination method for cloning with the flexibility of PCR to introduce modifications in the insert sequence. Moreover, this method allows the construction of chimerical DNA molecules associating two different elements, such as promoter-gene association or fusion proteins.

22 Claims, 6 Drawing Sheets

```
  1  aacgctagca tggatctcgg gccccaaata atgatttat tttgactgat agtgacctgt
 61  tcgttgcaac aaattgatga gcaatgcttt tttataatgc caactttgta caaaaaagca
121  ggcttcacaA TGGCCGCCGA GGAGGGAGTC GTGATCGCCT GCCACAACAA GGACGAGTTC
181  GACGCCCAGA TGACCAAGGC CAAGGAGGCC GGCAAAGTGG TCATAATTGA CTTCACTGCT
241  TCCTGGTGTG GCCCTTGCCG CTTCATCGCC CCAGTGTTCG CTGAATACGC CAAAAAGTTC
301  CCTGGTGCTG TCTTCCTGAA GGTTGATGTT GATGAGCTGA AGGAAGTTGC TGAAAAGTAC
361  AATGTCGAGG CAATGCCGAC CTTCCTATTC ATCAAGGATG GTGCTGAGGC TGACAAGGTC
421  GTTGGCGCCA GGAAGGATGA CCTCCAGAAC ACCATCGTGA AGCACGTCGG TGCCACTGCT
481  GCATCTGCTT CTGCCTAAga attctcgcag gcgcacccag ctttccttgta caagttggc
541  attataagaa agcattgctt atcaatttgt tgcaacgaac aggtcactat cagtcaaaat
601  aaaatcatta tttgccatcc agctgcagct ctggcccgtg tctcaaaatc tctgatgtta
```

FIGURE 2

```
  1 ggggacaagt ttgtacaaaa aagcaggctt cacaATGGCC GCCGAGGAGG GAGTCGTGAT
 61 CGCCTGCCAC AACAAGGACG AGTTCGACGC CCAGATGACC AAGGCCAAGG AGGCCGGCAA
121 AGTGGTCATA ATTGACTTCA CTGCTTCCTG G
```

FIGURE 3

```
  1  TGCGGACCGT GCCGCTTCAT CGCCCCAGTG TTCGCTGAAT ACGCCAAAAA GTTCCCTGGT
 61  GCTGTCTTCC TGAAGGTTGA TGTTGATGAG CTGAAGGAAG TTGCTGAAAA GTACAATGTC
121  GAGGCAATGC CGACCTTCCT ATTCATCAAG GATGGTGCTG AGGCTGACAA GGTCGTTGGC
181  GCCAGGAAGG ATGACCTCCA GAACACCATC GTGAAGCACG TCGGTGCCAC TGCTGCATCT
241  GCTTCTGCCT AAgaattctc gcaggcgcac ccagctttct tgtacaaagt ggtcccc
```

FIGURE 4

```
  1 attgatgagc aatgcttttt tataatgcca actttgtaca aaaaagcagg cttcacaATG
 61 GCCGCCGAGG AGGGAGTCGT GATCGCCCTGC CACAACAAGG ACGAGTTCGA CGCCCAGATG
121 ACCAAGGCCA AGGAGGCCGG CAAAGTGGTC ATAATTGACT TCACTGCTTC CTGGTGCGGA
181 CCGTGCCGCT TCATCGCCCC AGTGTTCGCT GAATACGCCA AAAAGTTCCC TGGTGCTGTC
241 TTCCTGAAGG TTGATGTTGA TGAGCTGAAG GAAGTTGCTG AAAAGTACAA TGTCGAGGCA
301 ATGCCCGACCT TCCTATTCAT CAAGGATGGT GCTGAGGCTG ACAAGTCGT TGGCGCCAGG
361 AAGGATGACC TCCAGAACAC CATCGTCGAAG CACCGTCGGTG ATCTGCTTCT
421 GCCTAAgaat tctcgcaggc gcacccagct ttcttgtaca aagttggcat tataagaaag
481 cattgcttat caatttgttg caacgaacag gtcactatca gtcaaaataa aatcattatt
```

FIGURE 5

METHOD FOR EASY CLONING AND SELECTION OF CHIMERIC DNA MOLECULES

FIELD OF INVENTION

The invention relates to a cloning method for efficient cloning of modified or chimeric or reconstructed DNA molecules. More particularly, there is provided a method to select the correct fragment to be cloned from a pool of incorrect fragments, simultaneously to the recombination cloning of that selected correct fragment.

BACKGROUND OF THE INVENTION

Recombination cloning methods, such as Gateway™ (Life Technologies, Inc., Paisley, UK) are typically used to clone only one DNA molecule into an entry vector. In certain cases, it may be desirable to create a chimeric or modified DNA molecule, consisting of two parts, for cloning in a Gateway™ entry vector. Examples of such chimeric molecules include suitable gene-promoter combinations, genes encoding a fusion protein, etc. Examples of modified DNA molecules include for example site directed mutants. Classical cloning techniques comprise the making of the chimeric molecule, for example a promoter-gene combination, in a separate intermediate construct, followed by the cloning of the chimeric molecule as a whole into the entry vector.

The Gateway™ cloning system was designed to introduce the DNA of interest via site specific recombination into an "entry clone", whereby the DNA molecule is cloned as such that it is easily introduced via another site specific recombination reaction into a subsequent set of "destination vectors". These latter vectors carry the necessary backbone sequences to successfully transform a particular host cell and to assure the desired expression of the cloned DNA of interest. Before the DNA molecule, for example the promoter-gene combination is introduced in the "entry clone", the gene must be operably linked to the promoter and the correct promoter-gene combination must be selected. Classical cloning steps to achieve this operably linkage, typically involve (i) cleavage of fragments via restriction enzymes or amplification of overlapping fragments via PCR techniques and (ii) subsequent assembling of the different fragments into an intermediary construct via ligation of the restriction enzyme sites or via assembly or "fill-in" PCR, (iii) analyzing the intermediary constructs and (iv) selecting the correct promoter-gene combination. From this intermediary construct the desired DNA molecule, here the promoter-gene combination will be PCR amplified as 1 whole, using two PCR primers that contain the suitable Gateway™ recombination sites. These recombination sites are compatible with the recombination sites of the acceptor plasmid (the entry clone or a destination clone of the Gateway™ system) and the amplified and purified DNA molecule as a whole will be recombined into the acceptor plasmid. One way to simplify this method would be to make the combination of the promoter-gene molecule simultaneously with the recombination cloning into the Gateway™ plasmid.

SUMMARY OF THE INVENTION

It is now shown in the present invention that a promoter-gene combination can be made and the same reaction mixture is used to clone the promoter-gene combination into a Gateway™ plasmid. This procedure encloses, two PCR reactions, combining the PCR products in the presence of a ligase, and using the ligation mixture in the recombination reaction with the acceptor plasmid. The end product is prone to contain only the correct combination of the two PCR fragments in the correct order and the correct orientation, flanked by two functional Gateway™ recombination sites. The method of the present invention thus offers a single-step procedure to select the correct combination of the PCR fragments and simultaneously cloning said correct combination. Accordingly, the present invention discloses a single step procedure to simultaneously combine, select and clone complex DNA molecules into a recombination acceptor plasmid. Therefore, according to a first embodiment, the invention provides a method for producing a modified and/or chimeric and/or reconstructed DNA molecule, composed of two parts, such method comprising the steps of:

(a) PCR amplification of each part of said two parts of said DNA molecule by means of two primer sets that build in a recombination site at the outer end of each PCR product (so to form two PCR products) and, (b) ligation of the two PCR products and, (c) recombination cloning of the ligated PCR products into the recombination vector.

In a particular embodiment of the invention, there is provided a method as described above for the production of a promoter-gene combination.

The outer ends of each PCR products, as used herein, are the ends that are not to be ligated to each other.

The present invention provides a method of obtaining chimeric DNA molecules as illustrated in FIG. 1. The linear DNA fragment "B1" contains a Gateway™ AttB1 site at one end (5'B1 end), and a second end (3'N1 end). The "B2" linear DNA fragment contains an 5'N2 end and a Gateway™ AttB2 site at the second end (3'B2 end). Both DNA pieces are produced by PCR, purified, phosphorylated, mixed and ligated. The ligation results in the production of a mixture of chimeric DNA fragments composed by "B1" and B2" units in various order and orientations. This mixture is directly, without any further purification step, submitted to the Gateway™ BP reaction using a Gateway™ compatible entry vector as an acceptor plasmid. Only chimeric DNA fragments containing the sequence "5'B1.3'N1-5'N2.3'B2" are transferred within the AttP1 and AttP2 sites of the entry vector. The final product is a Gateway™ entry clone that contains a DNA fragment "B1+B2" directionally inserted within the AttL1 and AttL2 Gateway™ sites, in the correct order and the correct orientation. This entry clone can then be used to transfer the B1B2 fragment into Gateway™ destination vectors using the LR reaction.

In the methods of the present invention, only one cloning step is necessary to construct a chimeric DNA molecule containing two DNA fragments in the desired order and orientation into a Gateway™ entry clone. The present invention eliminates the need for time-consuming classical cloning to produce such chimeric molecules (whereby modified DNA molecules may be obtained as a chimeric molecule) and therefore saves time and effort. Moreover, the invention substantially increases the versatility of the Gateway™ recombination cloning method. The method according to the present invention is also referred to as "combigate" method.

The procedure of the present invention can also be applied to make mutations into a DNA molecule and to simultaneously clone the mutated DNA molecule in the desired recombination vector. Therefore, the invention relates to a method for mutation of a nucleic acid molecule, compatible with high throughput cloning, comprising the steps of: (a) the design of two N and AttB primer sets (N1 and AttB1 primer set and N2 and AttB2 primer set) containing a mutation in their N1 or N2 primer and/or in their AttB1 or AttB2 primer, (b) amplifying two portions of that nucleic acid molecule with the above mentioned primer sets, whereby the mutation is incorporated in the sequence of these portions corresponding with the mutating primer(s), (c) reconstruction of the two fragments in a ligation reaction and (d) simultaneous selection and cloning of the reconstructed and mutated nucleic acid molecule directly in a recombination vector using the ligation product of step C in a recombination reaction. Accordingly, a particular embodiment of the invention provides a method as described above for the production of a mutated DNA molecule. In a particular embodiment the two primer sets as described above contain mutations in the N1 and N2 primers.

Advantageously, the procedure of the present invention can be applied to amplify large DNA-molecules and to simultaneously select the correct reconstruction of the original large DNA molecule and the simultaneous cloning of said large DNA molecule in the desired recombination vector. The classical cloning of very large sequences in one piece is sometimes cumbersome due to the presence of many cloning sites in the sequence, for example restriction enzyme recognition sites. For recombination cloning, the sequence always has to be amplified to incorporate the necessary recombination sites and it is known that PCR amplification of large sequences is sometimes difficult. The polymerase and the reaction conditions are often limiting to the number of base pairs that can be amplified. For example, sequences larger than 1 kb, 1.5 kb, 2 kb or 2.5 kb are difficult to be amplified with certain polymerases and/or in certain reaction conditions. Furthermore, the PCR amplification of large DNA sequences involves the risk of incorporating wrong base pairs due to the natural error rate or low fidelity of the polymerase, even when the polymerase is a polymerase mixture or even when the polymerase has proofreading capacity. The present invention offers the possibility to divide such large sequences in two parts, amplify it and clone it via recombination, said cloning being suitable for high throughput cloning and said method not requiring an extra cloning step.

According to a further embodiment of the invention, there is provided a method as described above for the cloning of a DNA molecule larger than 1 kb, or larger than 1.5 kb, such as fragments larger than 2 kb or larger than 2.5 kb.

BRIEF DESCRIPTION OF THE DRAWINGS

FIG. 2 shows the sequence of rice thioredoxin H in pDONR201. The thioredoxin H coding sequence is indicated in uppercase, the plasmid sequence in lowercase. The position of the N1 primer is single-underlined. The position of the N2 primer is double-underlined FIG. 3 shows the sequence of the "B1" PCR fragment for rice thioredoxin H mutagenesis. The thioredoxine H coding sequence is indicated in uppercase, the AttB1 sequence in lowercase. The N1 primer sequence is single-underlined.

FIG. 4 sets forth the sequence of the "B2" PCR fragment for rice thioredoxin H mutagenesis. The thioredoxine H coding sequence is indicated in uppercase, the AttB2 sequence in lowercase. The Rsr II site is in boldface. The N2 primer sequence is double-underlined FIG. 5 shows the sequence of the modified rice thioredoxin H in pDONR201. The thioredoxin H coding sequence is indicated in uppercase, the plasmid sequence in lowercase. The Rsr II site is in boldface. The sequence of the N1 primer is single-underlined. The sequence of the N2 primer is double-underlined

DETAILED DESCRIPTION OF THE INVENTION

Figure 1:
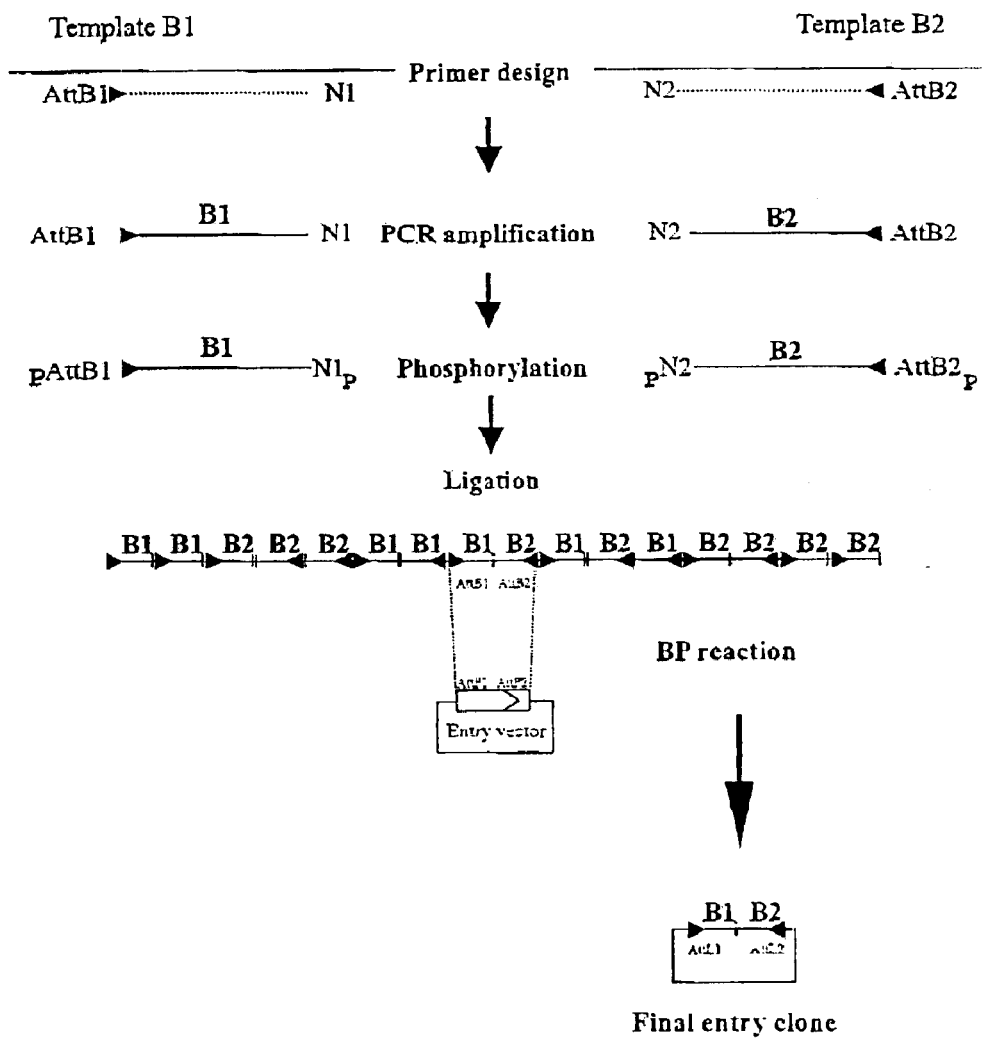
FIG. 1 is a schematic illustration of the recombination cloning procedure described in the invention, exemplified by using AttB1 and AttB2 sites of the Gateway™ system.

The general aim of the invention is to construct a chimeric B1-B2 DNA molecule from the fusion of a B1 and a B2 DNA molecule (FIG. 1). Two DNA fragments are amplified by PCR. Fragment B1 is amplified from the B1 template using forward primer 5'B1, that contains an AttB1 site, and reverse primer 3'N1. Fragment B2 is amplified from the B2 template using forward primer 5'N2 and reverse primer 3'B2, that contains an AttB2 site. Thus, each DNA fragment, 5 B1.3'N1 (B1) and 5'N2.3'B2 (B2) contains only one Gateway™ site for the BP reaction. None of the B1 or B2 molecules can be directly cloned into an entry vector using the HP reaction.

The 2 fragments are phosphorylated at their 5' ends with polynucleotide kinase, then mixed together and submitted to a DNA ligation. The resulting mixture contains a population of DNA molecules of different size, containing A and B fragments randomly joined together in any order, orientation and number. That population of DNA molecules is then directly, without additional selection or purification, submitted to the HP reaction using a Gateway™ entry vector as an acceptor plasmid. The BP clonase mix will specifically select and cleave out B1-B2 units with the structure 5'B1.3'N1-5'N2.3'B2 from the DNA molecules, and insert such units into the Gateway™ entry vector.

Examples for which the use of the procedure according to the invention is particularly useful include the construction of suitable promoter-gene combinations; the construction of genes encoding fusion proteins; the production of site-directed mutants and the cloning of large DNA fragments, for example larger than 1 kb, 1.5 kb, 2 kb, 2.5 kb.

For the production of site-directed mutations in any given gene, the site-directed mutant version of the gene is constructed as a chimeric molecule split near the mutation site. One (or both) of the N primers is designed containing the mutation(s) as desired, and has the appropriate length in order to continue to hybridize with the unmodified gene. Additionally or alternatively, the AttB primers can contain the mutation(s) as desired. A chimeric gene is then produced by the following steps: (a) using the primer(s) containing the mutation(s) for the PCR reaction, (b) further ligating the PCR fragment and (c) recombination cloning of the PCR fragments into a recombination acceptor plasmid according to the methods of the present invention.

The limiting factor in a recombination cloning is not the number of molecules that is presented to the recombination vector in the recombination reaction, but it is more the availability of the correct product amongst the number of incorrect molecules. To increase the ratio of correct molecules (i.e. molecules with correct recombination sites at the correct ends) versus incorrect molecules, the following steps can be incorporated in the process prior to the recombination step.

Several options can be used to implement the method according to the invention. Possible approaches include the following:

OPTION 1: Fragment Selection

The ligation step in the procedure as described above produces a population of molecules of various length. The length of these molecules depends on the number of copies of B1 and/or B2 fragments which they comprise. To further increase the overall efficiency of the BP cloning, one can select from gel electrophoresis only fragments that show a size similar to that of a B1-B2 molecule, comprising a single copy of B1 and a single copy of B2. This fragment selection is particular useful especially when the B1 and B2 fragments are of different size. In this case, there is a difference in length between the correct and the incorrect DNA molecules. However, even if B1 and B2 are of the same length, fragment selection as described above would allow to reduce the population of all the variant DNA molecules to only a few variants, namely, B1B1, B2B2, B1B2 and B2B1. When offering this selected fragment mixture to the recombination vector in the recombination reaction, the increased ratio correct/incorrect DNA fragment may render the recombination reaction more successful.

OPTION 2: Use of Phosphorylated N1 and N2 Primers

As described above, the two PCR fragments are phosphorylated at their 5' ends with polynucleotide kinase, then mixed together and submitted to a DNA ligation. As an alternative to this phosphorylation step and to Bias the ligation towards the ligation of the fragments in the exact order and orientation, the PCR products are phosphorylated only at their proximal ends. The amplification of B1 and B2 fragment can be performed using 5'-phosphorylated N1 and N2 primers. Subsequently, the B1 and B2 PCR products are not phosphorylated with polynucleotide kinase. Each PCR fragment is therefore phosphorylated only at its "N" extremity, and the ligation step will give only 5'B1.3'N1-P-P5'N2.3'B2 molecules that are ready to be cloned. This procedure may further increase the efficiency of the BP cloning.

OPTION 3: Direct Cloning into a Gateway Destination Vector

The amplification of B1 and B2 fragment can be performed using B1 and B2 primers containing an AttL1 and an AttL2 site, respectively, instead of the AttB sites. The procedure is identical to the one illustrated in FIG. 1 except that the B1+B2 unit is cloned using the LR reaction into a Gateway™ destination vector containing the AttR cassette. This allows the direct cloning of the chimerical DNA molecule into a final vector, i.e. an expression vector, without the necessity of a first step of cloning into an entry vector and a subsequent step of cloning into the destination vector. More generally, it is possible to use primers with AttB, AttP, AttL, AttR sites for the amplification, providing that the cloning vector bares the corresponding cassette, respectively with AttP, AttB, AttR, AttL sites.

OPTION 4: Cloning Using Nested PCR

After the ligation step, the population of DNA fragments can be submitted to PCR, using the 5'B1 and 3'B2 primers. Fragments with the structure 5'B1.N1-N1.5'B1, 3'B2.N2-N2.3'B2 and 5'B1.N1-N2.3'B2 are amplified preferentially. The PCR mixture is then used in a BP reaction. Only fragments with the structure 5'B1.N1-N2.3'B2, that bare both AttB1 and AttB2 sites can be cloned. This procedure could increase the efficiency of the BP cloning. More generally, the chimerical B1+B2 fragment can be constructed from any kind of linear DNA source (PCR fragments, restriction fragments, etc.), as long as adequate 5'B1 and 3'B2 primers have been defined for amplification of the correct B1+B2 molecule. This procedure can be used in conjunction with options 1, 2 and 3, as described above, for even further optimizations of the BP cloning.

The present invention further provides a method as described above, wherein there is no purification step between the ligation and the recombination cloning of the two PCR fragments.

Alternatively, according to the optional steps as described above, the present invention provides a method as described above, comprising an optional step of fragment selection between the ligation step and the recombination cloning step, and/or comprising an optional step of phosphorylation of the PCR fragments at their proximal end, prior to the ligation step and/or comprising an optional step of nested PCR on the ligation product, prior to the recombination cloning step.

The "proximal ends" of the PCR products are those ends of the PCR products that are to be ligated to each other. In a preferred embodiment of the invention, this phosphorylation is achieved during the PCR amplification of these PCR fragments, due to the use of two primer sets of which one of the primers, corresponding to the proximal end of the PCR fragment that need to be ligated to the proximal end of the other PCR fragment, is phosphorylated at it's 5' end.

The present invention provides a method for producing a modified or chimeric DNA molecule composed of two parts for cloning in a recombination vector, such method comprising the steps of PCR amplification of each part of the modified or chimeric DNA molecule by means of two primer sets that build in a recombination site at the outer ends of each PCR product followed by ligation of the two PCR products prior to cloning in the recombination vector. Only the correct combination (the correct order and the correct orientation) of the two desired DNA fragments will reconstruct into a functional recombination cassette comprising the two recombination sites in the correct order and the correct orientation. Therefore only that correct chimeric DNA will be cleaved out and inserted into the recombination acceptor vector.

Accordingly, the present invention provides a method as described above, wherein said two parts are cloned in a particular order and orientation.

The term "order" as used herein means the position of two parts determined when going from left to right in a double stranded linear DNA fragment or when going clockwise in a circular double stranded DNA fragment. For example the correct order of the fragment B1B2 is first B1 and than B2 when going from left to right in a double stranded linear DNA fragment or when going clockwise in a circular double stranded DNA fragment.

The term "orientation" as used herein is first the 5' site of a part and than the 3' site of said part when going from left to right in a double stranded linear DNA fragment or when going clockwise in a circular double stranded DNA fragment. For example the correct orientation of the B1 fragment in the B1B2 molecule is first the 5' site of B1 and than the 3' site of B1 when going from left to right in a double stranded linear DNA fragment or when going clockwise in a circular double stranded DNA fragment. The cloning in the correct order and orientation according to the above-described method of the invention is particularly useful if the modified and/or chimeric and/or reconstructed DNA molecule is not functional if the two parts are not ligated in the correct order and/or correct orientation. Accordingly, another embodiment of the present invention relates to a method as described above wherein said two parts are cloned in a particular order and orientation that are necessary for the intended function of the cloned DNA molecule.

In the PCR amplification as described above, recombination sites are built in only at the outer ends of the PCR products.

Accordingly, the present invention provides a method as described above, wherein a first primer set, amplifying a 5' part of said DNA molecule is designed to build in a recombination site at the 5' end of that DNA part and wherein a second primer set, amplifying a 3' portion of said DNA molecule, is designed to build a recombination site at the 3' end of that part.

In a more particular embodiment of the present invention there is provided a method as described above, wherein said recombination vector is a Gateway™ vector and wherein said recombination site is a Gateway™ recombination site and wherein said recombination cloning is a Gateway™ recombination reaction. The Gateway™ components (entry vectors, destination vectors, recombination sites) and Gateway™ reactions (recombination reactions) are described in detail by the provider of the Gateway™ system (Invitrogen, Life Technologies, Paisley, UK). In a particular embodiment of the invention said Gateway™ recombination site is an AttI, attB2, AttR1, AttR2, AttL1, AttL2 or AttP1 or AttP2 site.

In a particular embodiment of the invention, the Gateway™ recombination reaction is a BP or an LR recombination reaction according to the Gateway™ recombination system. A Gateway™ vector is a vector as provided by the Gateway™ cloning system. This system provides Gateway™ entry clones and Gateway™ destination clones. Accordingly, the invention further provides a method as described above, wherein said recombination vector is a Gateway™ entry clone.

An alternative embodiment of the invention is a method as described above, wherein said recombination vector is a Gateway™ destination clone.

The present invention further relates to a modified and/or chimeric and/or reconstructed DNA molecule obtained by the methods as described above.

A modified DNA molecule means a DNA molecule that is altered in its sequence compared to the original DNA sequence. This is for example a mutated DNA molecule. According to a further embodiment of the invention, there is provided a DNA molecule as described above, which is a mutated DNA molecule. A chimeric DNA molecule means a DNA molecule comprising at least two parts, which do not originally occur adjacent to each other in the same DNA molecule. In a particular embodiment, the invention provides a DNA molecule as described above, which is a promoter-gene combination A reconstructed DNA molecule means a DNA molecule that has been divided in parts and that has been rebuilt to form the original (or mutated) DNA molecule.

The following examples further illustrate the invention and are not intended to limit the scope thereof.

EXAMPLE 1

Introduction of a Rsr II Site Within the Rice Thioredoxin H Sequence

A Gateway™ entry clone pDONR201 (Life Technologies, Inc) containing the rice Thioredoxin H coding sequence in was used as a template for PCR amplification (FIG. 2). Standard PCR conditions were used: primers 1 $\mu$M, reaction buffer 1×, dNTP 250 $\mu$M, Platinum Pfx DNA polymerase (Life Technologies, Inc.) 0.2 U/$\mu$l, MgSO4 1 mM; 1 cycle of denaturation at 94° C. 5 min, followed by 30 cycles of denaturation at 94° C. 1 min—annealing at 40° C. 1 mm—elongation at 68° C. 2 min followed by 1 cycle of elongation at 68° C. 5 min.

The "B1" fragment was isolated by PCR using standard conditions (final volume 50 $\mu$l) with primers prm474 (B1) (SEQ ID NO 1): GGGGACAAGTTTGTACAAAAAAG-CAGGC TTCACAATGGCCGCCGAGGAGGGAGTCG TG, and prm595 (N1) (SEQ ID NO 2): CCAGGAAG-CAGTGAAGTCAATTATG. The "B2" fragment was isolated by PCR using standard conditions (final volume 50 $\mu$l) with primers prm598 (N2) (SEQ ID NO 3): TGCGGAC-CGTGCCGCTTCATCGCCCC (the Rsr II site is underlined) and prm475 (B2) (SEQ ID NO 4): GGGGAC-CACTTTGTACAAGAAAGCTGGGTGCGCCTGCGAG AATTCTTAGGCAG. Both fragments were purified from agarose gel using Qiaquick column (Qiagen Inc.) according to the instructions of the manufacturer (final volume 28 $\mu$l). The purified fragments (7 $\mu$l) were phosphorylated with T4 polynucleotide kinase (Promega) (ATP 1 $\mu$M, buffer 1 ×, T4 polynucleotide kinase 5 U, 1 h incubation at 37° C.). Equal volumes (7 $\mu$l) of the reaction mixtures were pooled and ligated using 14 $\mu$l of DNA ligase from Takara at 24° C. for 3 h, then inactivated at 65° C. for 10 min. The ligation product (2$\mu$l) was submitted to the Gateway BP reaction (Life Technologies, Inc.) using pDONR201 as an entry vector, following the instructions of the manufacturer (final volume 5 $\mu$l). The gateway reaction mixture was used to transform 50 $\mu$l of heat shock competent *E. coli* DH5a (Life Technologies, Inc.) according to the specifications of the producer. The bacteria were finally plated on kanamycin containing LB medium for selection.

Individual colonies were selected and amplified for plasmid preparations. The presence of the thioredoxin H insert was verified by restriction analysis. The complete Gateway™ cassette, including the AttL sites and the thioredoxin H insert was sequenced for verification. The sequence was identical to predicted sequence (FIGS. 3,4,5) A thioredoxin H containing a Rsr II site within the enzymatic active site was therefore obtained.

EXAMPLE 2

Promoter—GUS Fusion

Standard PCR conditions were: primers 1 $\mu$M, reaction buffer A 0.1×, buffer B 0.9×, dNTP 500 $\mu$M, elongase DNA polymerase (Life Technologies, Inc.) 0.2 U/$\mu$l; 1 cycle of denaturation at 94° C. 5 min followed by 35 cycles of denaturation at 94° C. 30 sec—annealing at 60° C. 30 sec—elongation at 68° C. 90 sec, followed by 1 cycle of elongation at 68° C. 5 min.

Figure 6:
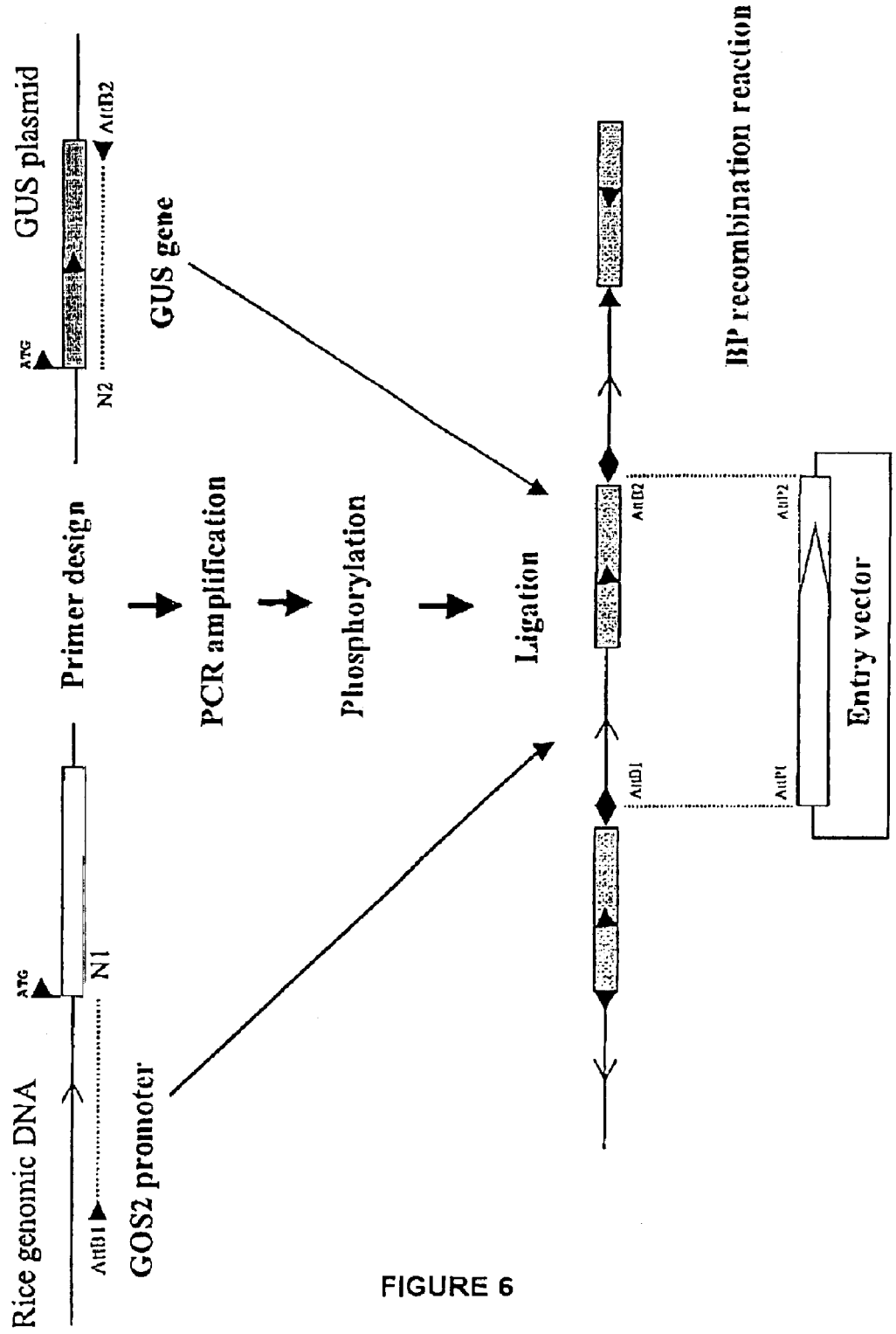
FIG. 6 is a schematic illustration of the association of the rice GOS2 promoter with the beta-glucuronidase GUS gene using the method of the invention.

The "B1" fragment, containing the rice GOS2 promoter and containing the 5' untranslated region up to the translation initiating ATG, was isolated from rice (*Oryza sativa* variety Nipponbare) genomic DNA by PCR using standard conditions (final volume 50 $\mu$l) with primers prm2200 (B1) (SEQ ID NO 5): GGGGACAAGTTTGTACAAAAAAG-CAGGCTAATGCG AAAAGTTTCTGCACCGT, and prm2432 (N1) (SEQ ID NO 6): GAACTTTGCTGGT GAAAGTGGC. The "B2" fragment, containing the complete GUS coding sequence, was isolated from the pOO25 plasmid bearing the beta-glucuronidase gene GUS with an intron by PCR using standard conditions (final volume 50 $\mu$l) with primers prm2203 (N2) (SEQ ID NO 7): ATGT-TACGTCCTGTAGAAACCCCAACC and prm0547 (B2) (SEQ ID NO 8): GGGGACCACTTTGTACAA-GAAAGCTGGGTTTGTTGATTCATTGTTTGCCT CC. Both PCR fragments were purified from agarose gel using Zymoclean™ kit (ZymoResearch Inc.) according to the instructions of the manufacturer (final volume 8 $\mu$l). The purified fragments (7 $\mu$l) were phosphorylated with T4 polynucleotide kinase (Promega) (ATP 1 $\mu$M, buffer 1×, T4 kinase 5 U, 1 h incubation at 37° C.). Equal volumes (5 $\mu$l) of the reaction mixtures were pooled and ligated using 10 $\mu$l of DNA ligase from Takara at 16° C. overnight. The ligation product (2 $\mu$l) was submitted to the Gateway™ BP reaction using pDONR201 as an entry vector (see FIG. 6), following the instructions of the manufacturer (final volume 5 µl). The Gateway™ reaction mixture was used to transform 50 µl of heat shock competent *E. coli* DH5a (Life Technologies, Inc.) according to the specifications of the producer. The bacteria were finally plated on kanamycin containing LB medium for selection.

Individual colonies were selected and amplified for plasmid preparations. The presence and the orientation the GOS2 promoter and the GUS gene was verified by restriction analysis and sequencing. The sequence of the boundary of the GOS2-GUS junction was also verified. The sequence of the promoter-gene combination was identical to that predicted.

What is claimed is:

1. A method for producing a modified and/or chimeric and/or reconstructed DNA molecule composed of two parts, and subsequent cloning thereof into a recombination vector, said method comprising the following steps performed in the following order:
   (a) PCR amplification of each part of said two parts of said DNA molecule by means of two primer sets that build in a recombination site at only one of the outer ends of each PCR product so as to form two PCR products;
   (b) ligation of the two PCR products; and
   (c) recombination cloning of the ligated PCR products into the recombination vector.

2. The method according to claim 1 for the production of a promoter-gene combination.

3. The method according to claim 1 for the production of a mutated DNA molecule.

4. The method according to claim 1 for the cloning of a DNA molecule larger than 1 kb, 1.5 kb, 2 kb or 2.5 kb.

5. The method according to any of claims 1 to 4 wherein a first primer set, amplifying a 5' part of said DNA molecule is designed to build in a recombination site at the 5' end of that DNA part and wherein a second primer set, amplifying a 3' portion of said DNA molecule, is designed to build a recombination site at the 3' end of that part.

6. The method according to any of claims 1 to 4, wherein said recombination vector is a vector which allows site specific recombination, and wherein said recombination site is a recombination site found in a recombination vector, and wherein said recombination cloning is performed using a recombination reaction.

7. The method according to any of claims 1 to 4, wherein there is no purification step between the ligation and the recombination cloning of the two PCR fragments.

8. The method according to any of claims 1 to 4, comprising an optional step of fragment selection between the ligation step and the recombination cloning step.

9. The method according to any of claims 1 to 4, comprising an optional step of phosphorylation of the PCR fragments at their proximal end, prior to the ligation step.

10. The method according to any of claims 1 to 4, comprising an optional step of nested PCR on the ligation product, prior to the recombination cloning step.

11. The method according to any of claims 1 to 4, wherein said recombination vector is a vector which allows site specific recombination.

12. The method according to any of claims 1 to 4, wherein said recombination vector is a vector which comprises backbone sequences to successfully transform a particular host cell and to express a cloned DNA of interest.

13. The method according to any of claims 1 to 4, wherein said two parts are cloned in a particular order and orientation.

14. The method according to claim 5 wherein said recombination vector is a vector which allows site specific recombination, wherein said recombination site is a recombination site found in a recombination vector, and wherein said recombination cloning is performed using a recombination reaction.

15. The method according to claim 5 wherein there is no purification step between the ligation and the recombination cloning of the two PCR fragments.

16. The method according to claim 5, comprising an optional step of fragment selection between the ligation step and the recombination cloning step.

17. The method according to claim 5 comprising an optional step of nested PCR the ligation product, prior to the recombination cloning step.

18. The method according to claim 8 comprising an optional step of nested PCR on the ligation product, prior to the recombination cloning step.

19. The method according to claim 5 further comprising an optional step of phosphorylation of the PCR fragments at their proximal end, prior to the ligation step.

20. The method according to claim 8 further comprising an optional step of phosphorylation of the PCR fragments at their proximal end, prior to the ligation step.

21. The method according to claim 6 wherein said recombination vector comprises at least one of an attB, attP, attR, or attL recombination site.

22. The method according to claim 11 wherein said recombination vector comprises at least one of an attB, attP, attR, or attL recombination site.

* * * * *

UNITED STATES PATENT AND TRADEMARK OFFICE
CERTIFICATE OF CORRECTION

PATENT NO. : 6,955,882 B2
DATED : October 18, 2005
INVENTOR(S) : Yves Hatzfield, Valerie Marie-Noelle Frankard and Anne-Marie Droual It is certified that error appears in the above-identified patent and that said Letters Patent is hereby corrected as shown below:

Column 4,
Lines 20 and 28, "HP" should read -- BP --.

Column 5,
Line 22, "Bias" should read -- bias --.

Column 7,
Line 17, "attl" should read -- attBl --.
Line 55, delete "in".
Line 64, "mm" should read -- min --.

Column 8,
Lines 6-7, should read -- TGCGGACCGTGCCGCTTCATCGGCCC TGCGGACCGTGCCGCTTCATCGCCCC --.
Line 20, "gateway" should read -- Gateway$^{TM}$ --.

Signed and Sealed this

Fourteenth Day of February, 2006

JON W. DUDAS
*Director of the United States Patent and Trademark Office*

SEQUENCE LISTING

```
<160> NUMBER OF SEQ ID NOS: 12

<210> SEQ ID NO 1
<211> LENGTH: 58
<212> TYPE: DNA
<213> ORGANISM: Artificial Sequence
<220> FEATURE:
<223> OTHER INFORMATION: Primer 474 (B1)

<400> SEQUENCE: 1
ggggacaagt ttgtacaaaa aagcaggctt cacaatggcc gccgaggagg gagtcgtg      58

<210> SEQ ID NO 2
<211> LENGTH: 25
<212> TYPE: DNA
<213> ORGANISM: Artificial Sequence
<220> FEATURE:
<223> OTHER INFORMATION: Primer 595 (N1)

<400> SEQUENCE: 2
ccaggaagca gtgaagtcaa ttatg                                          25

<210> SEQ ID NO 3
<211> LENGTH: 26
<212> TYPE: DNA
<213> ORGANISM: Artificial Sequence
<220> FEATURE:
<223> OTHER INFORMATION: Primer 598 (N2)

<400> SEQUENCE: 3
tgcggaccgt gccgcttcat cgcccc                                         26

<210> SEQ ID NO 4
<211> LENGTH: 53
<212> TYPE: DNA
<213> ORGANISM: Artificial Sequence
<220> FEATURE:
<223> OTHER INFORMATION: Primer 475 (B2)

<400> SEQUENCE: 4
ggggaccact ttgtacaaga aagctgggtg cgcctgcgag aattcttagg cag           53

<210> SEQ ID NO 5
<211> LENGTH: 52
<212> TYPE: DNA
<213> ORGANISM: Artificial Sequence
<220> FEATURE:
<223> OTHER INFORMATION: Primer 2200 (B1)

<400> SEQUENCE: 5
ggggacaagt ttgtacaaaa aagcaggcta atccgaaaag tttctgcacc gt            52

<210> SEQ ID NO 6
<211> LENGTH: 22
<212> TYPE: DNA
<213> ORGANISM: Artificial Sequence
```

```
<220> FEATURE:
<223> OTHER INFORMATION: Primer 2432 (N1)

<400> SEQUENCE: 6
gaactttgct ggtgaaagtg gc                                              22

<210> SEQ ID NO 7
<211> LENGTH: 27
<212> TYPE: DNA
<213> ORGANISM: Artificial Sequence
<220> FEATURE:
<223> OTHER INFORMATION: Primer 2203 (N2)

<400> SEQUENCE: 7
atgttacgtc ctgtagaaac cccaacc                                         27

<210> SEQ ID NO 8
<211> LENGTH: 52
<212> TYPE: DNA
<213> ORGANISM: Artificial Sequence
<220> FEATURE:
<223> OTHER INFORMATION: Primer 0547 (B2)

<400> SEQUENCE: 8
ggggaccact ttgtacaaga aagctgggtt tgttgattca ttgtttgcct cc             52

<210> SEQ ID NO 9
<211> LENGTH: 659
<212> TYPE: DNA
<213> ORGANISM: Artificial Sequence
<220> FEATURE:
<223> OTHER INFORMATION: Thioredoxin of Oryza sativa in vector pDONR201

<400> SEQUENCE: 9
aacgctagca tggatctcgg gccccaaata atgattttat tttgactgat agtgacctgt     60
tcgttgcaac aaattgatga gcaatgcttt tttataatgc caactttgta caaaaaagca    120
ggcttcacaa tggccgccga ggagggagtc gtgatcgcct ccacaacaa ggacgagttc     180 gacgcccaga tgaccaaggc caaggaggcc ggcaaagtgg tcataattga cttcactgct    240
tcctggtgtg gcccttgccg cttcatcgcc ccagtgttcg ctgaatacgc caaaaagttc    300
cctggtgctg tcttcctgaa ggttgatgtt gatgagctga aggaagttgc tgaaaagtac    360
aatgtcgagg caatgccgac cttcctatta tcaaggatgg tgctgaggct gacaaggtcg    420
ttggcgccag gaaggatgac ctccagaaca ccatcgtgaa gcacgtcggt gccactgctg    480
catctgcttc tgcctaagaa ttctcgcagg cgcacccagc tttcttgtac aaagttggca    540
ttataagaaa gcattgctta tcaatttgtt gcaacgaaca ggtcactatc agtcaaaata    600
aaatcattat ttgccatcca gctgcagctc tggcccgtgt ctcaaaatct ctgatgtta    659

<210> SEQ ID NO 10
<211> LENGTH: 151
<212> TYPE: DNA
<213> ORGANISM: Artificial Sequence
<220> FEATURE:
<223> OTHER INFORMATION: sequence of the "B1" PCR fragment for Oryza
      sativa thioredoxin H
      mutagenesis

<400> SEQUENCE: 10
ggggacaagt ttgtacaaaa aagcaggctt cacaatggcc gccgaggagg gagtcgtgat     60
cgcctgccac aacaaggacg agttcgacgc ccagatgacc aaggccaagg aggccggcaa    120
```

```
agtggtcata attgacttca ctgcttcctg g                              151
```

<210> SEQ ID NO 11
<211> LENGTH: 297
<212> TYPE: DNA
<213> ORGANISM: Artificial Sequence
<220> FEATURE:
<223> OTHER INFORMATION: sequence of the "B2" PCR fragment for Oryza
      sativa thioredoxin H
      mutagenesis

<400> SEQUENCE: 11

```
tgcggaccgt gccgcttcat cgccccagtg ttcgctgaat acgccaaaaa gttccctggt    60
gctgtcttcc tgaaggttga tgttgatgag ctgaaggaag ttgctgaaaa gtacaatgtc   120
gaggcaatgc cgaccttcct attcatcaag gatggtgctg aggctgacaa ggtcgttggc   180
gccaggaagg atgacctcca gaacaccatc gtgaagcacg tcggtgccac tgctgcatct   240
gcttctgcct aagaattctc gcaggcgcac ccagctttct tgtacaaagt ggtcccc      297
```

<210> SEQ ID NO 12
<211> LENGTH: 540
<212> TYPE: DNA
<213> ORGANISM: Artificial Sequence
<220> FEATURE:
<223> OTHER INFORMATION: Modified thioredoxin of Oryza sativa in vector
      pDONR201

<400> SEQUENCE: 12

```
attgatgagc aatgcttttt tataatgcca actttgtaca aaaaagcagg cttcacaatg    60
gccgccgagg agggagtcgt gatcgcctgc cacaacaagg acgagttcga cgcccagatg   120
accaaggcca aggaggccgg caaagtggtc ataattgact tcactgcttc ctggtgcgga   180
ccgtgccgct tcatcgcccc agtgttcgct gaatacgcca aaaagttccc tggtgctgtc   240
ttcctgaagg ttgatgttga tgagctgaag gaagttgctg aaaagtacaa tgtcgaggca   300
atgccgacct tcctattcat caaggatggt gctgaggctg acaaggtcgt tggcgccagg   360
aaggatgacc tccagaacac catcgtgaag cacgtcggtg ccactgctgc atctgcttct   420
gcctaagaat tctcgcaggc gcacccagct ttcttgtaca agttggcat tataagaaag   480 cattgcttat caatttgttg caacgaacag gtcactatca gtcaaataa aatcattatt   540
```